US008716286B2

(12) United States Patent
Bellingham et al.

(10) Patent No.: US 8,716,286 B2
(45) Date of Patent: May 6, 2014

(54) CRYSTALLINE FORMS OF (3R,6R)-3-(2,3-DIHYDRO-1H-INDEN-2-YL)-1-[(1R)-1-(2,6-DIMETHYL-3-PYRIDINYL)-2-(4-MORPHOLINYL)-2-OXOETHYL]-6-[(1S)-1-METHYLPROPYL]-2,5-PIPERAZINEDIONE

(75) Inventors: Richard Bellingham, Kent (GB);
Andrew Mark Buswell, Kent (GB);
Victoria Ironmonger, Kent (GB);
Michael Urquhart, Kent (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/504,681

(22) PCT Filed: Oct. 28, 2010
(Under 37 CFR 1.47)

(86) PCT No.: PCT/IB2010/003221
§ 371 (c)(1),
(2), (4) Date: Apr. 27, 2012

(87) PCT Pub. No.: WO2011/051814
PCT Pub. Date: May 5, 2011

(65) Prior Publication Data
US 2013/0109690 A1 May 2, 2013

Related U.S. Application Data

(60) Provisional application No. 61/256,594, filed on Oct. 30, 2009.

(51) Int. Cl.
*A61K 31/535* (2006.01)
*C07D 413/14* (2006.01)

(52) U.S. Cl.
USPC ........................ 514/235.8; 544/121

(58) Field of Classification Search
USPC ........................ 514/235.8; 544/121
See application file for complete search history.

(56) References Cited

U.S. PATENT DOCUMENTS

| 4,596,819 | A | 6/1986 | Nicolaides et al. |
| 5,464,788 | A | 11/1995 | Bock et al. |
| 5,817,751 | A | 10/1998 | Szardenings et al. |
| 7,550,462 | B2 | 6/2009 | Borthwick et al. |
| 7,919,492 | B2 | 4/2011 | Borthwick et al. |
| 8,202,864 | B2 | 6/2012 | Borthwick et al. |
| 2005/0148572 | A1 | 7/2005 | Borthwick et al. |
| 2007/0149524 | A1 | 6/2007 | Liddle |
| 2007/0185162 | A1 | 8/2007 | Borthwick et al. |
| 2007/0208031 | A1 | 9/2007 | Borthwick et al. |
| 2013/0253188 | A1 | 9/2013 | Borthwick et al. |

FOREIGN PATENT DOCUMENTS

| DE | 3830096 A1 | 3/1990 |
| GB | 2326639 A | 12/1998 |
| WO | 9937304 A1 | 7/1999 |
| WO | 9938844 A1 | 8/1999 |
| WO | 9947549 A1 | 9/1999 |
| WO | 03053443 A1 | 7/2003 |
| WO | 2005000311 A1 | 1/2005 |
| WO | 2005000840 A1 | 1/2005 |
| WO | 2006000399 A1 | 1/2006 |
| WO | 2006000400 A1 | 1/2006 |
| WO | 2006000759 A1 | 1/2006 |
| WO | 2006067462 A1 | 6/2006 |

OTHER PUBLICATIONS

Caira; "Crystalline Polymorphism of Organic Compounds"; Topics in Current Chemistry; 1998; vol. 198; pp. 163-208.
Akerlund; Prog. Brain. Res.; 2002; vol. 139; pp. 359-365.
Banker et al.; Modern Pharmaceutics, 3rd Ed.; 1996; p. 596.
Clement et al.; Brain Oxytocin Receptors Mediate Ejaculation Elicited by 7-hydroxy-2-(di-N-propylamino)tetralin(7-OH-DPAT) in Anaesthetized Rats; British Journal of Pharmacology; 2008; vol. 154; pp. 1150-1159.
Grigorash et al.; Chem. Heterocycl. Compound; 1977; vol. 13, No. 12; pp. 1280-1281.
Kolasa et al.; J. Org. Chem.; 1990; vol. 55, No. 6; pp. 1711-1721.
Pettibone et al.; Drug Development Research; 1993; vol. 30, No. 3; pp. 129-142.
Stella; Pro Drugs: An Overview and Definition; Pro Drugs as Novel Drug Delivery Systems; 1975; Chapter 1; pp. 1-115.
Testa et al.; Pure Appl. Chem.; 2004; vol. 76; pp. 907-914.
Tsatsaris et al.; Drugs; 2004; vol. 64(4) Abstract; pp. 375-382.
Vippagunta et al.; Advanced Drug Delivery Reviews; 2001; vol. 48; pp. 3-26.
Waldinger; Premature Ejaculation: Definition and Drug Treatment; Drugs; 2007; vol. 67, No. 4; pp. 547-568.
Wolff; Burger's Medicinal Chemistry, 5th Ed., Part 1; 1995; pp. 975-977.
Wyatt et al.; Bioorganic Med. Chem. Letters; 2001; vol. 11, No. 10; pp. 1301-1305.
Office Action dated Jun. 13, 2008 for U.S. Appl. No. 11/630,179.
Office Action dated Oct. 1, 2013 for EP Application No. 10807364.4.

*Primary Examiner* — Rebecca Anderson
(74) *Attorney, Agent, or Firm* — Kathryn L. Coulter

(57) ABSTRACT

The present invention relates to crystalline forms of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate salt and pharmaceutical compositions thereof. Also disclosed are processes for the preparation the above compounds and methods for use thereof.

5 Claims, 7 Drawing Sheets

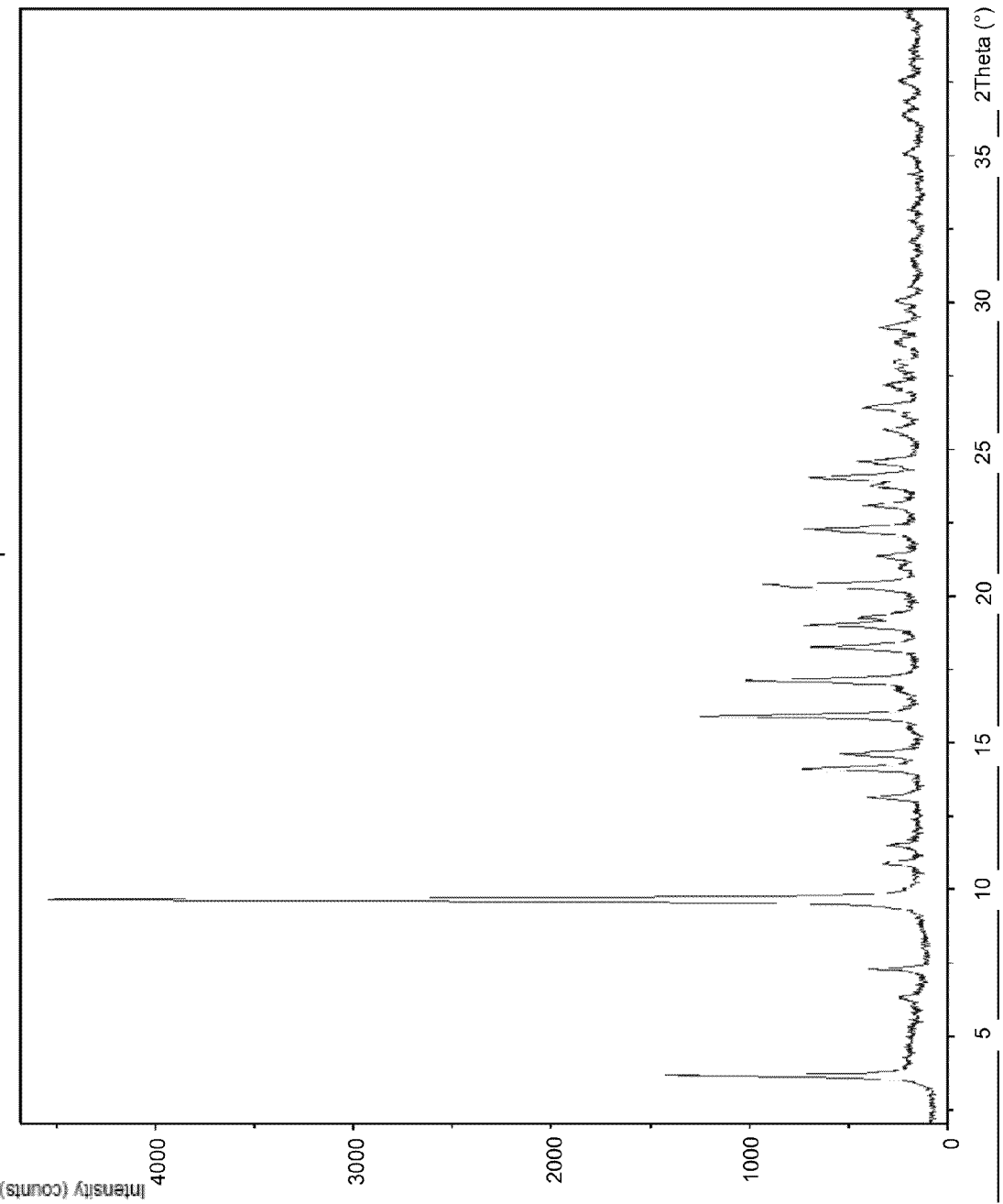
FIG. 1 – Compound A-Form 1

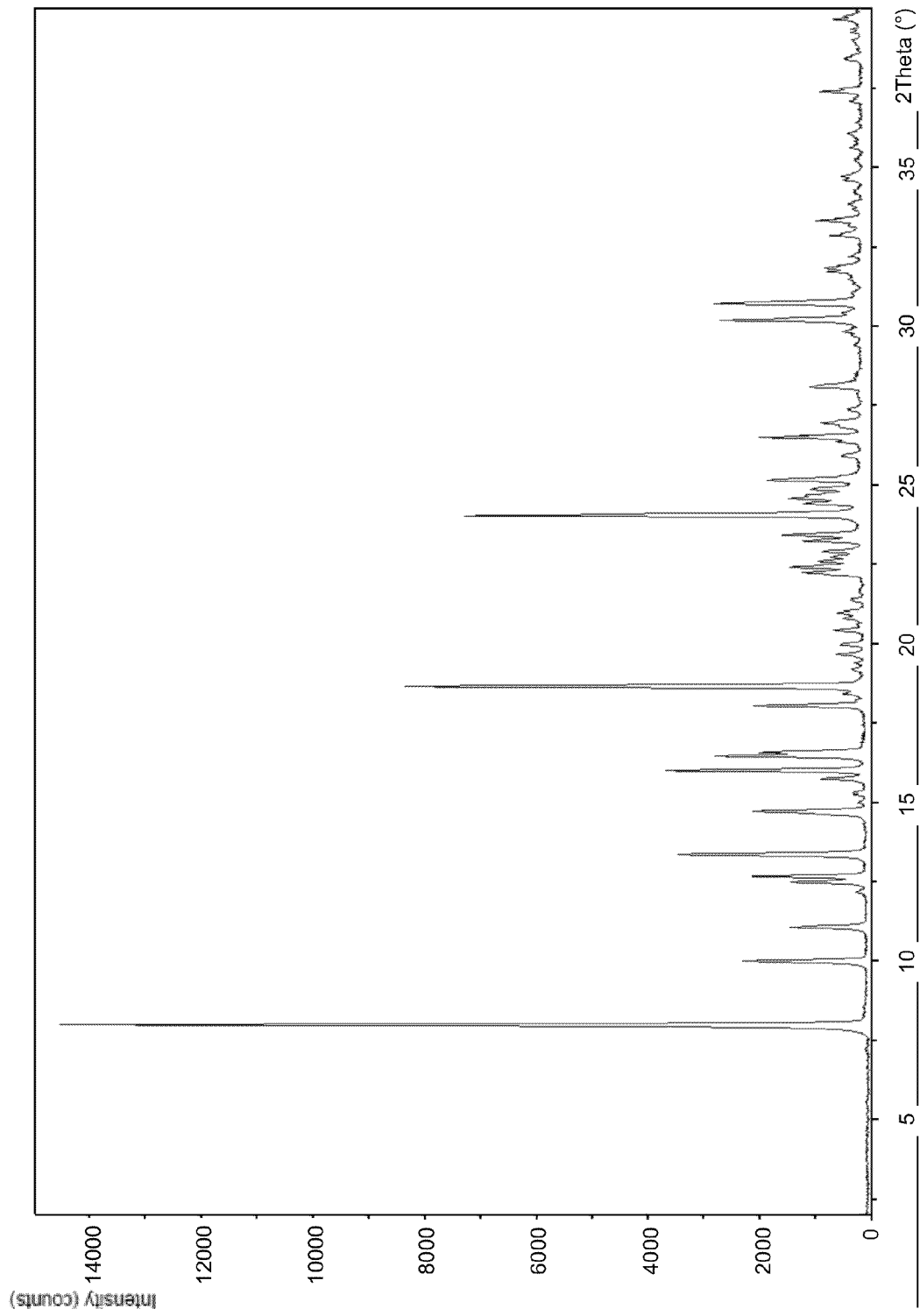
FIG. 2 – Compound A-Form 2

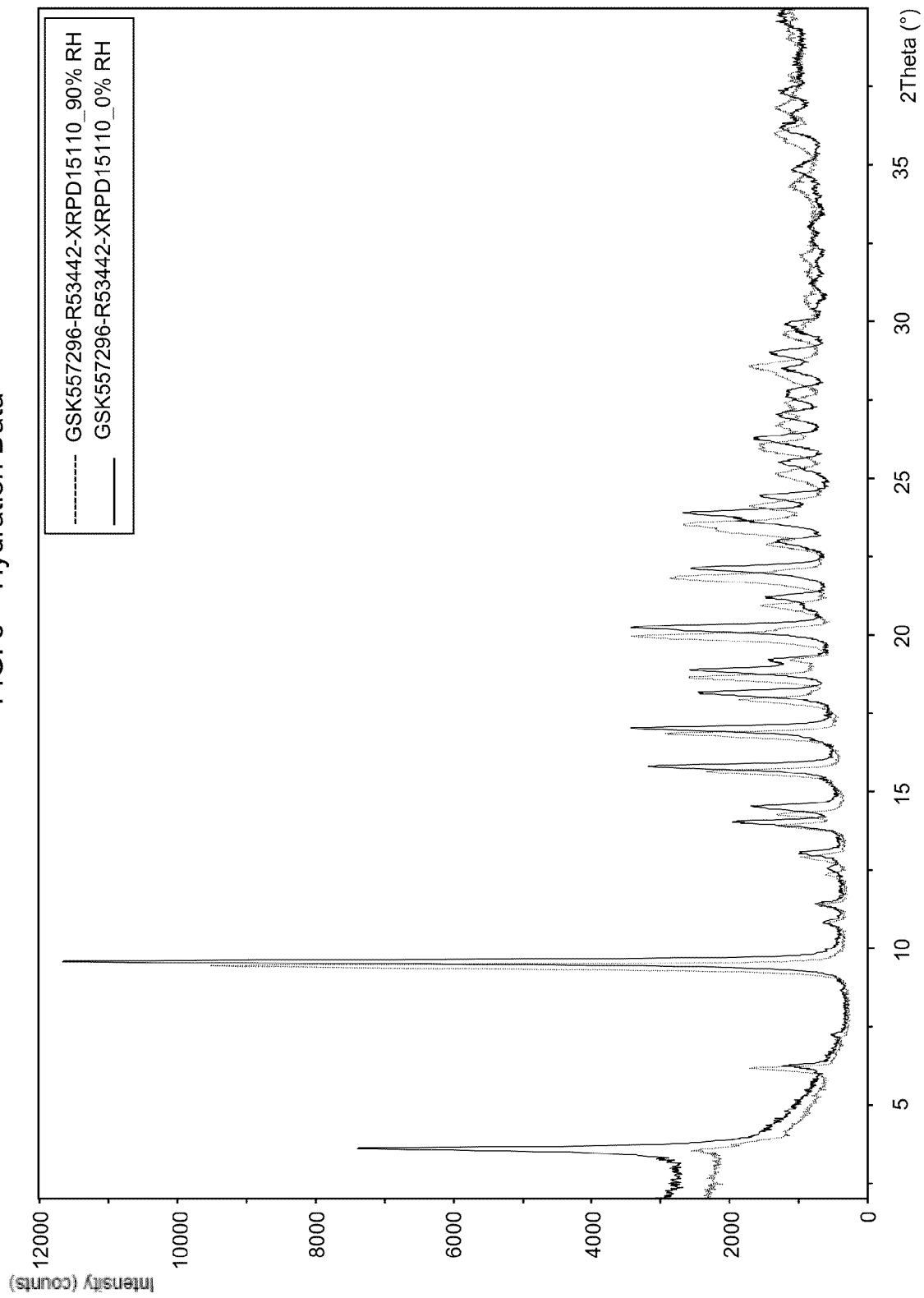
FIG. 3 – Hydration Data

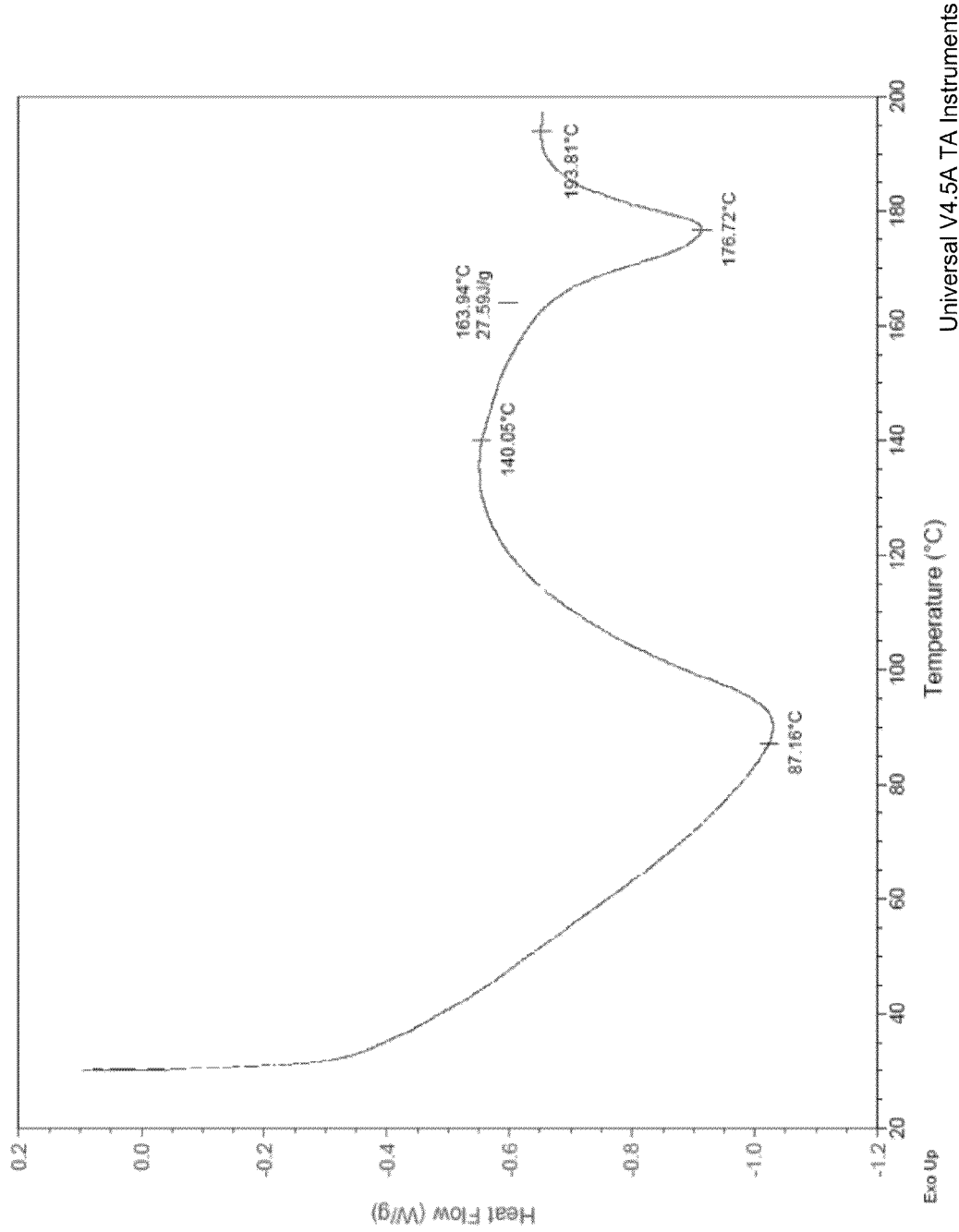
FIG. 4 – DSC Trace of Form 1

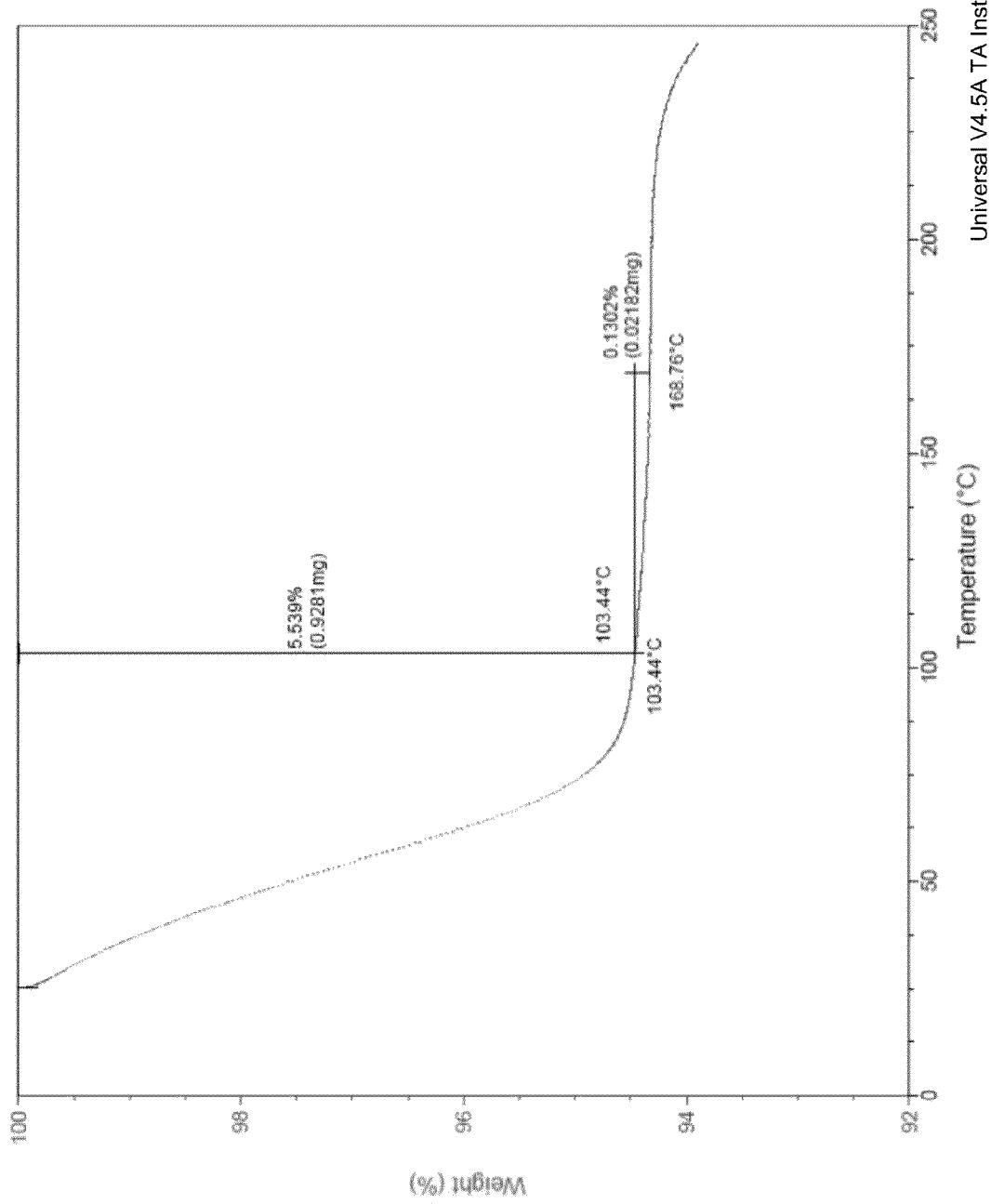
FIG. 5 – TGA Trace of Form 1

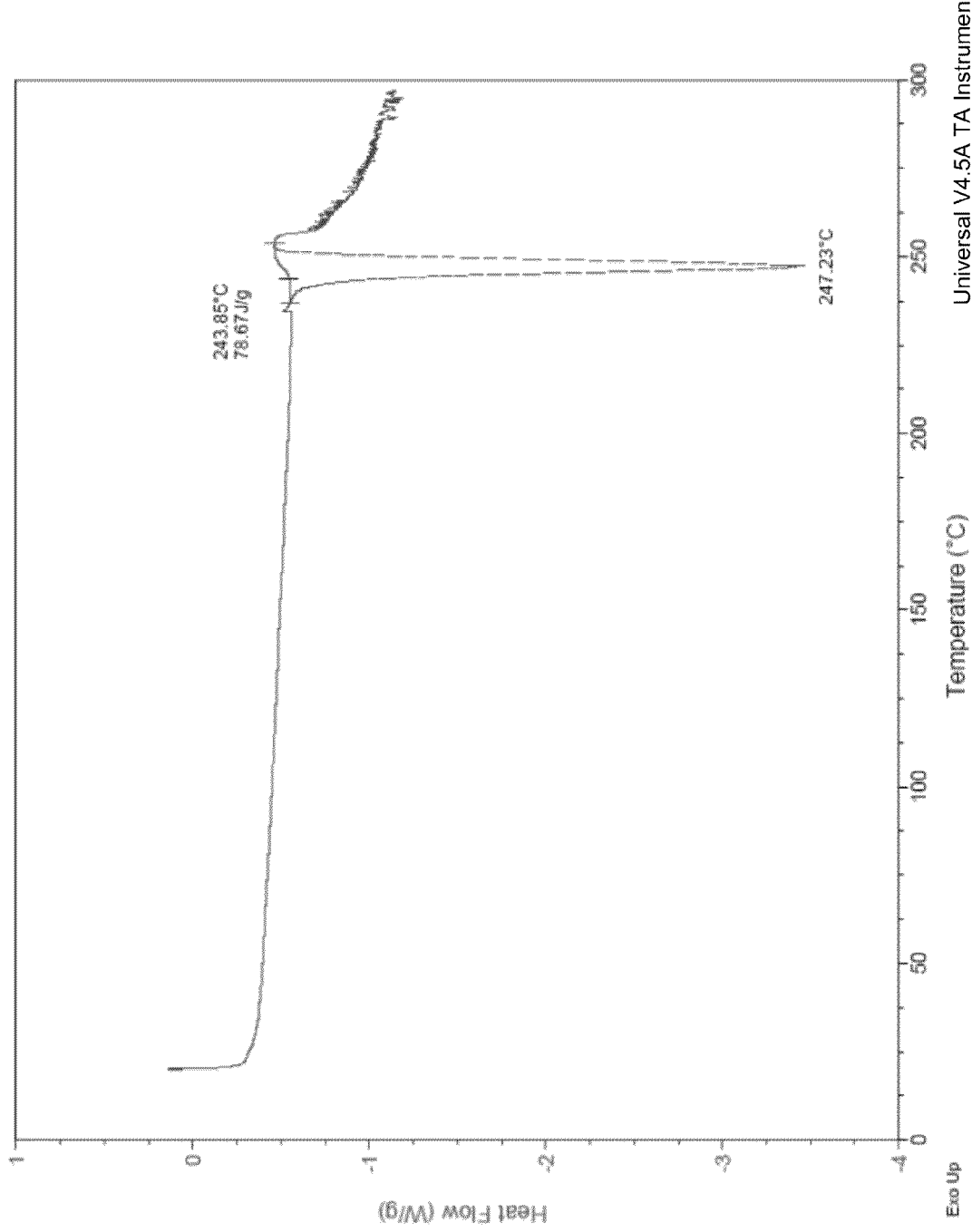
FIG. 6 – DSC Trace of Form 2

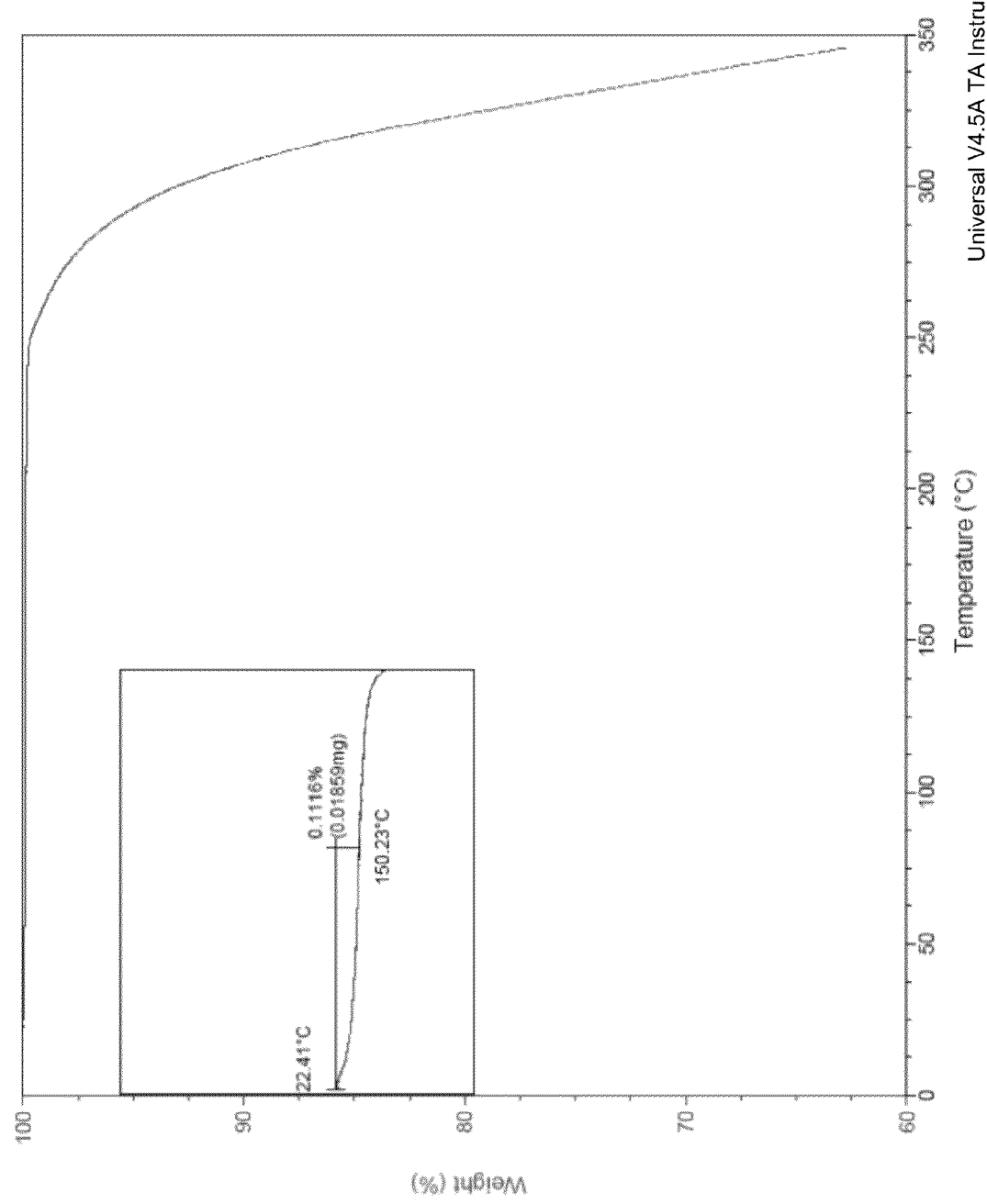

CRYSTALLINE FORMS OF (3R, 6R)-3-(2,3-DIHYDRO-1H-INDEN-2-YL)-1-[(1R)-1-(2,6-DIMETHYL-3-PYRIDINYL)-2-(4-MORPHOLINYL)-2-OXOETHYL]-6-[(1S)-1-METHYLPROPYL]-2,5-PIPERAZINEDIONE

CROSS-REFERENCE TO RELATED APPLICATIONS

This application is filed pursuant to 35 U.S.C. §371 as a United States National Phase Application of International Patent Application No. PCT/IB2010/003221 filed Oct. 28, 2010, which claims priority from Provisional Application No. 61/256,594 filed Oct. 30, 2009.

FIELD OF THE INVENTION

This invention relates to novel crystalline forms that are selective antagonist of oxytocin receptor, to pharmaceutical compositions containing them, to processes for their preparation, and to their use in therapy for the treatment of diseases mediated through oxytocin.

BACKGROUND OF THE INVENTION

In the pursuit of a developable form of a solid, orally-administered pharmaceutical compound, a number of specific features are sought. Although an amorphous form of a pharmaceutical compound may be developed, compounds having high crystallinity are generally preferred. Often such highly crystalline compounds are salts. It is greatly desired that such a salt would also possess the following features: good stability, good aqueous solubility (preferably >1 mg/mL), good in vivo oral bioavailability, and capability of being obtained in good yield (preferably >50%). However, whether and in which salt form a pharmaceutical compound can form a crystalline solid are highly unpredictable.

The mechanisms of oxytocin are described in U.S. Pat. No. 6,914,160. In man, oxytocin but not vasopressin plasma concentrations are significantly raised at or around ejaculation. Oxytocin does not induce ejaculation itself; this process is 100% under nervous control via 1-adrenoceptor/sympathetic nerves originating from the lumbar region of the spinal cord. The systemic pulse of oxytocin may have a direct role in the peripheral ejaculatory response. It could serve to modulate the contraction of ducts and glandular lobules throughout the male genital tract, thus influencing the fluid volume of different ejaculate components for example. Oxytocin releases centrally into the brain could influence sexual behavior, subjective appreciation of arousal (orgasm) and latency to subsequent ejaculation. Accordingly, the compounds of the present invention can be useful in treating premature ejaculation.

Pre-term births/labour (between 24 and 37 weeks) causes about 60% of infant mortality/morbidity. The density of uterine oxytocin receptors increases significantly by >100 fold during pregnancy and peaks in labour (pre-term and term). Hormone oxytocin is a potent contractor of the uterus and is used for the induction or augmentation of labour. It is believed that a compound which inhibits the uterine actions of oxytocin e.g. oxytocin antagonists, should be useful for the prevention or control of pre-term labour. Endogenous oxytocin peptide can be used clinically to induce labour in pregnant women, and atosiban, an oxytocin antagonist, is an established acute treatment to delay the onset of pre-term labour. Oxytocin is also known to be associated with other disease conditions. Oxytocin antagonists may be useful to delay labour prior to elective caesarean section or transfer of the patient to a tertiary care centre, treatment of sexual dysfunction (male and female), particularly premature ejaculation, obesity, eating disorders, congestive heart failure, arterial hypertension, liver cirrhosis, nephritic or ocular hypertension, obsessive-compulsive disorder and neuropsychiatric disorders.

International patent application WO 03/053443 describes a class of diketopiperazine derivatives which exhibit a particularly useful level of activity as selective oxytocin antagonists.

International Application No. PCT/EP2005/006760, having an International filing date of Jun. 10, 2005 and published as US Publication No. US2007254888A1 the entire disclosure of which is hereby incorporated by reference, describes a number of highly potent oxytocin inhibitors which are indicated as useful in the treatment of diseases or conditions mediated through the action of oxytocin. Specifically disclosed in that application is (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione (Example 3, hereinafter Compound A) and its preparation methods.

Since the discovery of Compound A, significant efforts have been put into identifying crystalline salt forms that are more suitable for pharmaceutical development; however, many acid addition salts do not form crystalline salt. The present inventors have now discovered two novel crystalline forms of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate salt, hereinafter Compound A-Form 1 and Compound A-Form 2.

SUMMARY OF THE INVENTION

This invention relates to novel crystalline forms of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate salt, processes for their preparation, pharmaceutical compositions containing them and to their use in medicine. The benzenesulfonate salt of Compound A is represented by the following structure:

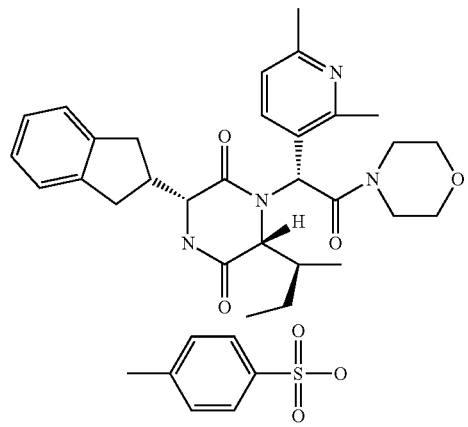

In one aspect, the present invention provides a crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate hydrate, wherein said crystalline form provides an X-ray powder diffraction pattern substantially in accordance with FIG. 1.

In another aspect, the invention encompasses a crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate hydrate, wherein said crystalline form is characterized by an X-ray powder diffraction pattern comprising the peaks:

| Diff Angle (°2Theta) | d-Spacing |
|---|---|
| 3.7 ± 0.1 | 24.2 |
| 7.3 ± 0.1 | 12.2 |
| 9.6 ± 0.1 | 9.2 |
| 14.1 ± 0.1 | 6.3 |
| 17.1 ± 0.1 | 5.2 |

In an additional aspect, the invention includes a crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate hydrate, wherein said compound is characterized by an X-ray powder diffraction pattern substantially in accordance with FIG. 1.

In certain aspects, the invention encompasses a crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate, wherein said compound is characterized by an X-ray powder diffraction pattern substantially in accordance with FIG. 2.

In one aspect, the invention also provides a crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate, wherein said crystalline form is characterized by an X-ray powder diffraction pattern comprising the peaks:

| Diff Angle (°2Theta) | d-Spacing |
|---|---|
| 8.0 ± 0.1 | 11.1 |
| 10.0 ± 0.1 | 8.9 |
| 16.4 ± 0.1 | 5.4 |
| 18.6 ± 0.1 | 4.8 |

In a particular embodiment, the invention provides a pharmaceutical composition comprising a crystalline form of the invention and a pharmaceutically acceptable carrier.

In another embodiment, the invention provides a method of treating premature ejaculation or pre-term labour comprising administering to a human in need thereof an effective amount of a crystalline form according to the invention.

In additional embodiment, the invention provides a crystalline form of the invention for use in therapy.

In particular embodiments, the invention relates to a crystalline form of the invention for use in the treatment of premature ejaculation or pre-term labour.

In certain embodiments, the inventions relates to the use of a crystalline form according to the invention in the manufacture of a medicament for the treatment of premature ejaculation or pre-term labour.

BRIEF DESCRIPTION OF THE DRAWINGS

FIG. 1 shows an X-ray powder diffraction pattern of Compound A-Form 1.

FIG. 2 shows an X-ray powder diffraction pattern of Compound A-Form 2.

FIG. 3 shows the variation that can be experienced in the XRPD pattern of Form 1 as a result of varying water content.

FIG. 4 shows the differential scanning calorimetry trace of Form 1.

FIG. 5 shows the thermogravimetric analysis trace of Form 1.

FIG. 6 shows the differential scanning calorimetry trace of Form 2.

FIG. 7 shows the thermogravimetric analysis trace of Form 2.

DETAILED DESCRIPTION OF THE INVENTION

Following significant efforts involving a large number of screening experiments, many acid addition salts of Compound A failed to provide a crystalline solid under the conditions employed. Two crystalline forms of the benzenesulfonate salt (a.k.a besylate) of the above mentioned compound were found to have the characteristics of a developable solid form.

This invention relates to novel crystalline forms of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate Form 1.

This invention relates to novel crystalline forms of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate Form 2.

The term "solvates" refers to crystalline forms wherein solvent molecules are incorporated into the crystal lattice during crystallization. Solvates may include water or non-aqueous solvents such as ethanol, dimethyl sulfoxide, acetic acid, ethanolamine, and ethyl acetate. Solvates, wherein water is the solvent molecule incorporated into the crystal lattice, are typically referred to as "hydrates". Hydrates include stoichiometric hydrates (e.g. a monohydrate), as well as compositions containing variable amounts of water (e.g. channel hydrate). When a disclosed compound is named, it is to be understood that the compound, including solvates (particularly, hydrates) thereof, may exist in crystalline forms. The compound, or solvates (particularly, hydrates) thereof, may also exhibit polymorphism (i.e. the capacity to occur in different crystalline forms). These different crystalline forms are typically known as "polymorphs." It is to be understood that when named, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

One embodiment of the present invention is directed to Compound A-Form 1", providing an X-ray powder diffraction pattern substantially in accordance with FIG. 1.

Another embodiment of the present invention is directed to a crystalline form of Compound A-Form 1, providing an X-ray powder diffraction pattern providing diffraction lines (°2θ) at about 3.7, 6.3, 7.3, 9.6, 10.9, 11.5, 13.1, 14.1, 14.6, 15.9, 16.7, 17.1, 18.2, 19.0, 19.2, 20.4, 21.3, 22.3, 23.1, 23.7, 24.0, 24.5, 26.4, 27.2, 29.1. More particularly, another embodiment of the present invention is directed to a crystalline form of Compound A-Form 1, providing an X-ray powder diffraction pattern providing characteristic diffraction angles (°2θ) at about 3.7, 9.6, 17.1, 18.2, and 19.0.

In one aspect, the invention encompasses a crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate hydrate, wherein said crystalline form is characterized by an X-ray powder diffraction pattern comprising the peaks:

TABLE A

| Diff Angle (°2Theta) | d-Spacing |
|---|---|
| 3.7 ± 0.1 | 24.2 |
| 7.3 ± 0.1 | 12.2 |
| 9.6 ± 0.1 | 9.2 |
| 14.1 ± 0.1 | 6.3 |
| 17.1 ± 0.1 | 5.2 |

Another embodiment of the present invention is directed to a crystalline form of Compound A (hereinafter "Compound A-Form 2"), providing an X-ray powder diffraction pattern substantially in accordance with FIG. 2.

Another embodiment of the present invention is directed to a crystalline form of Compound A-Form 2, providing an X-ray powder diffraction pattern providing diffraction angles (°2θ) at about 5.5, 8.0, 10.0, 11.0, 12.1, 12.5, 12.6, 13.3, 14.7, 15.2, 15.7, 16.0, 16.4, 16.6, 18.0, 18.6, 19.6, 20.0, 20.4, 21.0, 22.1, 22.2, 22.4, 22.6, 22.9, 23.2, 23.4, 24.0, 24.4, 24.5, 24.7, 24.8, 25.1, 26.5, 28.0, 30.2, 30.7, 33.3, 37.4. More particularly, another embodiment of the present invention is directed to a crystalline form of Compound A-Form 2, providing an X-ray powder diffraction pattern providing characteristic diffraction angles (°2θ) at about 8.0, 10.0, 12.5, 12.6, 13.3, 16.4, 16.6, 18.0, 18.6.

In a certain aspect, the invention provides a crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate, wherein said crystalline form is characterized by an X-ray powder diffraction pattern comprising the peaks:

TABLE B

| Diff Angle (°2Theta) | d-Spacing |
|---|---|
| 8.0 ± 0.1 | 11.1 |
| 10.0 ± 0.1 | 8.9 |
| 16.4 ± 0.1 | 5.4 |
| 18.6 ± 0.1 | 4.8 |

It is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1 or 2 provided herein is an XRPD pattern that would be considered by one skilled in the art to represent a compound possessing the same crystal form as the compound that provided the XRPD pattern of FIG. 1 or 2. That is, the XRPD pattern may be identical to that of FIG. 1 or 2, or more likely it may be somewhat different (FIG. 3 shows the variation that can be experienced in the XRPD pattern of Form 1 as a result of varying water content). Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of a (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate, with FIG. 1 and, using expertise and knowledge in the art, readily determine whether the XRPD pattern of the sample is substantially in accordance with the XRPD pattern of Compound A-Form 1. If the XRPD pattern is substantially in accordance with FIG. 1, the sample form can be readily and accurately identified as having the same form as Compound A-Form 1. Similarly, a person skilled in the art is capable of determining if a given diffraction angle (expressed in °2θ) obtained from an XRPD pattern is at about the same position as a value presented herein. See FIG. 3 showing the variation of peak position and intensity that can occur with water content in the XRPD pattern of Form 1.

"Compound(s) of the invention" means (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate salt and solvates (particularly, hydrates) thereof, as described herein above, as well as all crystalline forms of said compounds, specifically the crystalline forms defined herein as Compound A-Form 1, or Compound A-Form 2.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

Suitable physiologically acceptable salts of Compound A include acid addition salts formed with physiologically acceptable inorganic acids or organic acids. Examples of such acids include hydrochloric acid, hydrobromic acid, nitric acid, phosphoric acid, sulfuric acid, sulfonic acids e.g. methanesulfonic, ethanesulfonic, benzenesulfonic and p-toluenesulfonic, citric acid, tartaric acid, lactic acid, pyruvic acid, acetic acid, succinic acid, fumaric acid and maleic acid.

It will further be appreciated that the amount of a compound of the invention required for use in treatment will vary with the nature of the condition being treated, the route of administration and the age and the condition of the patient and will be ultimately at the discretion of the attendant physician. In general, however, doses employed for adult human treatment will typically be in the range of 2 to 1000 mg per day, dependent upon the route of administration.

Thus for parenteral administration a daily dose will typically be in the range 2 to 50 mg, preferably 5 to 25 mg per day. For oral administration a daily dose will typically be within the range 10 to 1000 mg, e.g. 50 to 500 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) and/or pharmaceutically acceptable salts or solvates thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, vaginal or rectal administration.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in the conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

The compositions according to the invention may contain between 0.1-99% of the active ingredient, conveniently from 1-50% for tablets and capsules and 3-50% for liquid preparations.

The advantageous pharmacokinetic profile of the compounds of the invention is readily demonstrated using conventional procedures for measuring the pharmacokinetic properties of biologically active compounds.

The compounds of the invention and pharmaceutically acceptable derivatives thereof may be prepared by the processes described hereinafter, said processes constituting a further aspect of the invention. In the following description, the groups are as defined above for compounds of the invention unless otherwise stated.

In addition to the procedure described herein, Compound A may be prepared according to the disclosure of WO2006000399 (US2007254888A1).

Acid addition salts of Compound A may be prepared by conventional means, for example, by treating a solution of the compound in a suitable solvent such as dichloromethane or acetone, with a suitable solution of the appropriate inorganic or organic acid.

The following examples are illustrative, but not limiting of the embodiments of the present invention.

EXPERIMENTAL

Process Scheme

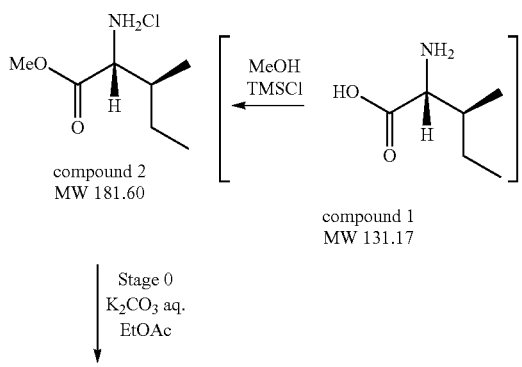

-continued
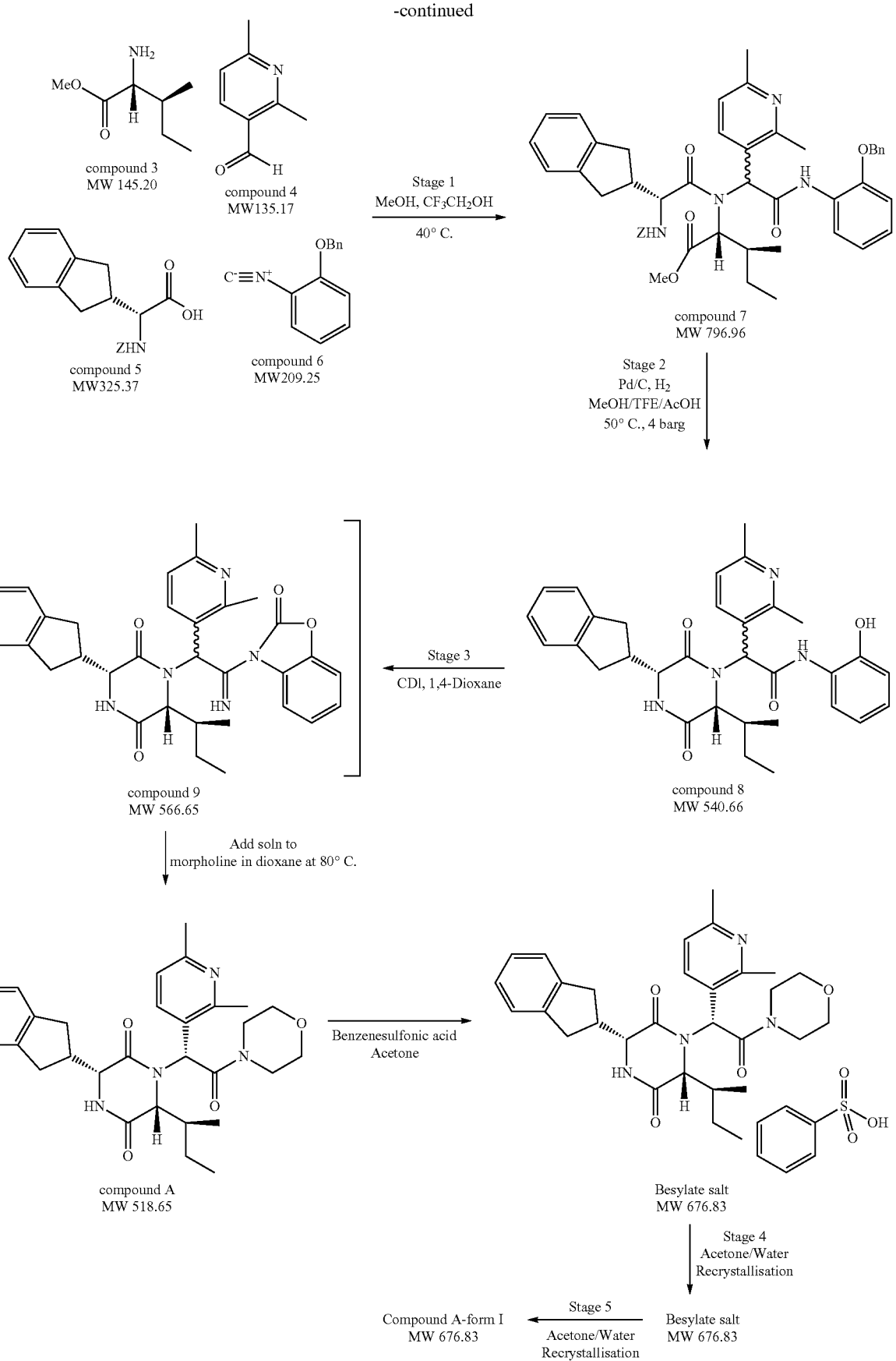

Process Description for Isolation of Compound A-Form 1

Stage 0 methyl d-alloisoleucinate hydrochloride (Compound 2) was charged to ethyl acetate. A solution of potassium carbonate in water was then added. The mixture was then stirred vigorously at room temperature for 1 hour. The two layers were separated and the aqueous layer further extracted with ethyl acetate. The organic layers were combined and washed with brine. The organic layers were then concentrated in vacuo and filtered to yield methyl D-alloisoleucinate (Compound 3) as a pale yellow oil.

Stage 1

2,6-dimethyl-3-pyridinecarbaldehyde (Compound 4) in methanol at ambient temperature was treated with D-alloisoleucinate (Compound 3) in methanol followed by 2,2,2-trifluoroethanol and the reaction mixture was warmed to 40° C. When formation of the intermediate imine (methyl N-[(2,6-dimethyl-3-pyridinyl)methylidene]-D-alloisoleucine) was complete Compound 5 was added followed by 1-isocyano-2-[(phenylmethyl)oxy]benzene (Compound 6) and the reaction mixture was stirred at 40° C. until formation of Compound 7 was deemed complete.

Stage 2

Palladium on carbon catalyst was treated with a solution of Compound 7 in methanol and 2,2,2-trifluoroethanol and diluted with acetic acid. The vessel was purged with nitrogen and the reaction mixture warmed to 50° C. and hydrogenated at 4.0-4.5 barg. When the reaction was deemed complete it was cooled to ambient temperature and the catalyst removed by filtration and washed through with methanol. The organic solution of 2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N-(2-hydroxyphenyl)acetamide (Compound 8) was concentrated at reduced pressure and then diluted with iso-propyl acetate and concentrated at reduced pressure. The residue was diluted with iso-propyl acetate and washed with aqueous ammonia. The aqueous phase was separated and extracted into another portion of iso-propyl acetate. The combined organic phases were washed with water, concentrated by distillation at reduced pressure, diluted with iso-propyl acetate and concentrated by distillation at reduced pressure, to leave a concentrated solution of 2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N-(2-hydroxyphenyl)acetamide (Compound 8). The product was finally dissolved in 1,4-dioxane for the next stage and stored into drums.

Stage 3

Solution of 2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N-(2-hydroxyphenyl)acetamide (Compound 8) in 1,4-dioxane was treated with 1,1'-carbonyl diimidazole at ambient temperature to form a solution containing (3R,6R)-3-(2,3-dihydro-1H-inden-2-yl)-1-[1-(2,6-dimethyl-3-pyridinyl)-2-oxo-2-(2-oxo-1,3-benzoxazol-3(2H)-yl)ethyl]-6-[(1S)-1-methylpropyl]-2,5-piperazinedione (Compound 9). In a separate vessel morpholine in 1,4-dioxane was heated to 80-85° C. The solution containing (3R,6R)-3-(2,3-dihydro-1H-inden-2-yl)-1-[1-(2,6-dimethyl-3-pyridinyl)-2-oxo-2-(2-oxo-1,3-benzoxazol-3(2H)-yl)ethyl]-6-[(1S)-1-methylpropyl]-2,5-piperazinedione (Compound 9) was slowly added to the morpholine in 1,4-dioxane. The reaction mixture was stirred for one hour at 80-85° C. and cooled before concentration by distillation at reduced pressure. The concentrated solution of Compound A was diluted with iso-propyl acetate and washed with aqueous sodium hydroxide followed by water. The iso-propyl acetate solution of COMPOUND A was then concentrated by distillation at reduced pressure and cooled to ambient temperature. The concentrated solution of Compound A was then diluted with acetone and treated with benzenesulfonic acid and seed crystals were added and the reaction mixture stirred until crystallisation occurred. The slurry of Compound A besylate was heated to 50° C., a temperature cycle was performed, and finally the slurry was cooled to −10° C. and isolated by filtration. The filter cake was washed with cold acetone (−10° C.) to give Compound A besylate (intermediate grade) as a wet cake.

Yield: 44% from Compound 5

39% from Compound 5

Stage 4

Compound A besylate (intermediate grade wet cake, Compound A besylate) was suspended in acetone (17.4 vol including acetone content of wet cake) and heated to 55-60° C. Water (0.66 vol) was added until dissolution was observed. The reaction mixture was then filtered into another vessel and the lines washed through with acetone (3.2 vol). The temperature of the reaction mixture was adjusted to 45-50° C. before the addition of seed crystals (0.00025 wt). When crystallisation was complete the reaction mixture was cooled to 20-25° C. and stirred at 20-25° C. for 30 mins. The reaction mixture was heated to 45-50° C. and stirred at 45-50° C. for 30 mins. The reaction mixture was cooled to 20-25° C. and stirred at 20-25° C. for 30 mins. The reaction mixture was heated to 45-50° C. and stirred at 45-50° C. for 30 mins. The reaction mixture was cooled to −3-2° C. over 4.5 h and stirred for at least 1 h before the product was isolated by filtration. The wet cake was washed with acetone at 0° C. (3×3.1 vol) and blown dry before being unloaded. COMPOUND A besylate was dried at 50° C. under vacuum for 3 days. Compound A besylate was then milled.

Yield: 66%

Stage 5

Compound A besylate (OBU-D-02) was suspended in acetone (8 vol) and water (1.1 vol) and heated to 48-52° C. until dissolution was observed. The reaction mixture was then filtered into another vessel and the lines washed through with acetone (2 vol). The reaction mixture was cooled to 20-25° C. before the addition of Form 1 seed crystals (0.0025 wt). When crystallisation was complete the reaction mixture was cooled to 0-5° C. over 1 h and stirred at 0-5° C. for 30 mins. The reaction mixture was heated to 20-25° C. and stirred at 20-25° C. for 30 mins. The reaction mixture was cooled to 0-5° C. over 1 h and stirred at 0-5° C. for 30 mins. The reaction mixture was heated to 20-25° C. and stirred at 20-25° C. for 30 mins. The reaction mixture was cooled to −12-−8° C. over 3.5 h and stirred for 15 h before the product was isolated by filtration. The wet cake was washed with acetone at −10° C. (2×3 vol) and blown dry before being unloaded. Compound A besylate was dried at ambient temperature under vacuum for 6 days with a wet nitrogen bleed to afford Form 1. Compound A besylate was then milled. Yield: 67%

Recrystallisation of Compound A Besylate Anhydrate (Form 2)

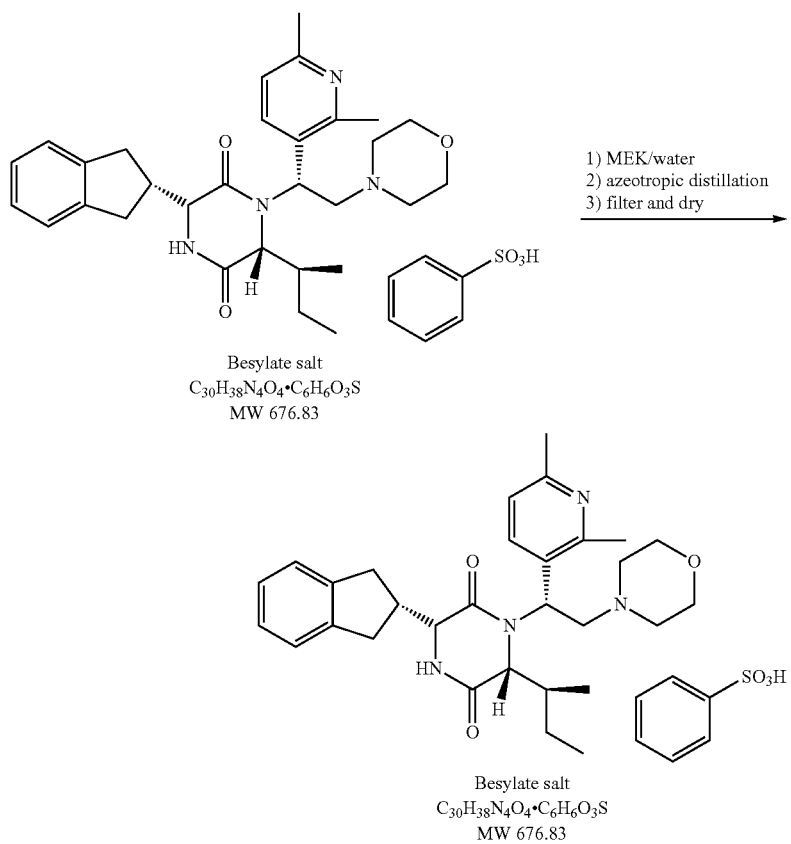

COMPOUND A besylate is charged to the vessel and treated with methyl ethyl ketone (MEK) (8 vol) and water (0.35 vol) and the solution heated until dissolution is observed (ca. 55-60° C.). The solution is then filtered and recharged to the vessel. Pressure is then reduced to 650 mbar and the reaction mixture heated further to distil out solvent. MEK is added at the same rate as solvent is removed by distillation keeping the reaction mixture volume constant. After 4 volumes of MEK have been added the reaction mixture is treated with Form 2 seed crystals (2% wt) and the distillation continued in the same manner until another 7 volumes of MEK has been added. The vacuum is then released to an atmospheric pressure of nitrogen and the temperature of the reaction mixture adjusted to 65° C. The reaction mixture is then filtered and washed with pre heated MEK (2 vol at 65° C.). The purified COMPOUND A besylate anhydrate is then sucked dry and dried further in a vacuum oven at 65° C. at 100 mbar with a nitrogen bleed.

Yield 89%

NMR data is the same for Forms 1 and 2.

1H NMR (500 MHz, DMSO-$d_6$) δppm 0.71-0.80 (m, 6H) 0.87-0.98 (m, 1H) 1.31 (br. S, 1H) 1.69 (br. S, 1H) 2.68 (s, 3H) 2.69 (s, 3H) 2.72-2.79 (m, 1H) 2.80-2.87 (m, 1H) 2.88-3.01 (m, 3H) 3.18-3.25 (m, 1H) 3.27-3.33 (m, 1H) 3.38-3.46 (m, 1H) 3.47-3.52 (m, 1H) 3.53-3.57 (m, 1H) 3.60-3.71 (m, 3H) 3.83 (dd, J=9.46, 3.15 Hz, 1H) 3.89 (br. S, 1H) 6.10 (br. S, 1H) 7.11-7.14 (m, 2H) 7.19-7.23 (m, 2H) 7.30-7.35 (m, 3H) 7.59-7.63 (m, 2H) 7.67 (d, J=7.25 Hz, 1H) 8.12 (br. S, 1H) 8.50 (d, J=3.78 Hz, 1H)

The X-ray powder diffraction pattern of this material is shown in FIG. 1 and a summary of the diffraction angles, d-spacings, and relative intensities is given in Table I. Data were acquired according to the following parameters:

Scan range: 2-40 °2θ
Generator power: 40 kV, 45 mA
Radiation Source: Cu Kα
Scan type: Continuous
Time per step: 31.75 s
Step size: 0.0167 °2θ per step
Sample Rotation: 1 s revolution time
Incident Beam optics: nickel filter, 0.02 radian soller slits, 10 mm beam mask, automatic divergence slits (set to irradiated length of 10 mm), beam knife.
Diffracted Beam optics: automatic anti scatter slit (set to irradiated length of 10 mm, slits 0.02 radian soller
Detector Type: Philips X'Celerator RTMS (Real Time Multi Strip)

TABLE I

| Form 1 | |
|---|---|
| Diff. Angle [°2θ] | d-spacing [Å] |
| 3.7 | 24.2 |
| 6.3 | 14.0 |
| 7.3 | 12.2 |
| 9.6 | 9.2 |
| 10.9 | 8.1 |
| 11.5 | 7.7 |

TABLE I-continued

Form 1

| Diff. Angle [°2θ] | d-spacing [Å] |
|---|---|
| 13.1 | 6.7 |
| 14.1 | 6.3 |
| 14.6 | 6.1 |
| 15.9 | 5.6 |
| 16.7 | 5.3 |
| 17.1 | 5.2 |
| 18.2 | 4.9 |
| 19.0 | 4.7 |
| 19.2 | 4.6 |
| 20.4 | 4.4 |
| 21.3 | 4.2 |
| 22.3 | 4.0 |
| 23.1 | 3.9 |
| 23.7 | 3.8 |
| 24.0 | 3.7 |
| 24.5 | 3.6 |
| 26.4 | 3.4 |
| 27.2 | 3.3 |
| 29.1 | 3.1 |

TABLE 2

Form 2 (anhydrate)

| Diff. Angle [°2θ] | d-spacing [Å] |
|---|---|
| 5.5 | 16.0 |
| 8.0 | 11.1 |
| 10.0 | 8.9 |
| 11.0 | 8.0 |
| 12.1 | 7.3 |
| 12.5 | 7.1 |
| 12.6 | 7.0 |
| 13.3 | 6.6 |
| 14.7 | 6.0 |
| 15.2 | 5.8 |
| 15.7 | 5.6 |
| 16.0 | 5.6 |
| 16.4 | 5.4 |
| 16.6 | 5.4 |
| 18.0 | 4.9 |
| 18.6 | 4.8 |
| 19.6 | 4.5 |
| 20.0 | 4.4 |
| 20.4 | 4.4 |
| 21.0 | 4.2 |
| 22.1 | 4.0 |
| 22.2 | 4.0 |
| 22.4 | 4.0 |
| 22.6 | 3.9 |
| 22.9 | 3.9 |
| 23.2 | 3.8 |
| 23.4 | 3.8 |
| 24.0 | 3.7 |
| 24.4 | 3.7 |
| 24.5 | 3.6 |
| 24.7 | 3.6 |
| 24.8 | 3.6 |
| 25.1 | 3.5 |
| 26.5 | 3.4 |
| 28.0 | 3.2 |
| 30.2 | 3.0 |
| 30.7 | 2.9 |
| 33.3 | 2.7 |
| 37.4 | 2.4 |

The differential scanning calorimetry trace of Form 1 is shown in FIG. 4. Data were acquired on a TA instruments Q1000 Differential Scanning Calorimeter. The sample was heated from 30° C. to 300° C. at 10° C./min. The thermogravimetric analysis trace of this material is shown in FIG. 5. Data were acquired on a TA instruments Q500 Thermogravimetric Analyzer. The sample was heated from 30° C. to 300° C. at 10° C./min.

The differential scanning calorimetry trace of Form 2 is shown in FIG. 6. Data were acquired on a TA instruments Q1000 Differential Scanning Calorimeter. The sample was heated from 30° C. to 300° C. at 10° C./min. The thermogravimetric analysis trace of this material is shown in FIG. 7. Data were acquired on a TA instruments Q500 Thermogravimetric Analyzer. The sample was heated from 30° C. to 300° C. at 10° C./min.

Biological Assays and Activity

Compounds of the present invention can be tested according to the description of International Publication No. WO2006000399 (US2007254888A1).

The invention claimed is:

1. A crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate, wherein said crystalline form provides an X-ray powder diffraction pattern substantially in accordance with FIG. 1.

2. A crystalline form of (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione benzenesulfonate, wherein said crystalline form is characterized by an X-ray powder diffraction pattern comprising the peaks:

| Diff Angle (°2Theta) | d-Spacing |
|---|---|
| 3.7 ± 0.1 | 24.2 |
| 7.3 ± 0.1 | 12.2 |
| 9.6 ± 0.1 | 9.2 |
| 14.1 ± 0.1 | 6.3 |
| 17.1 ± 0.1 | 5.2. |

3. A pharmaceutical composition comprising the crystalline form according to claim 2 and a pharmaceutically acceptable carrier.

4. A method of treating pre-term labour comprising administering to a human the crystalline form according to claim 2.

5. A method of treating premature ejaculation comprising administering to a human the crystalline form according to claim 2.

* * * * *